United States Patent [19]

Bird et al.

[11] Patent Number: 4,980,493
[45] Date of Patent: Dec. 25, 1990

[54] PROCESS FOR PREPARING BENZONITRILES

[75] Inventors: Graham Bird, Ascot Vale; Donald Harney, East St Kilda; Errol McGarry, Eltham North; Matthew Bolte, Romsey, all of Australia

[73] Assignee: ICI Australia Limited, Victoria, Australia

[21] Appl. No.: 25,547

[22] Filed: Mar. 13, 1987

[30] Foreign Application Priority Data

Mar. 13, 1986 [AU] Australia ............................. PH5011

[51] Int. Cl.$^5$ ........................................... C07C 255/50
[52] U.S. Cl. ................................................... 558/414
[58] Field of Search ......................................... 558/414

[56] References Cited

PUBLICATIONS

Morrison et al., Org. Chem., 2nd Ed., pp. 589–591, 601–603, 667, 671–672 (1970).

Primary Examiner—Robert W. Ramsuer
Assistant Examiner—J. Richter
Attorney, Agent, or Firm—Cushman, Darby & Cushman

[57] ABSTRACT

The invention relates to a process for the preparation of a compound of formula I

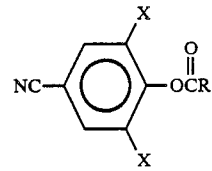

R is alkyl, and X is bromine or iodine which process comprises:
  reacting a compound of formula II in a two phase system, said system comprising an aqueous phase and an organic phase comprising a water immiscible solvent, with an acylating agent of formula III or IV in the presence of a base catalyst.

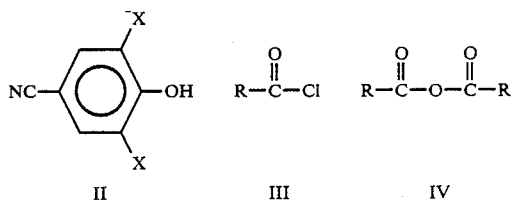

16 Claims, No Drawings

PROCESS FOR PREPARING BENZONITRILES

This invention relates to a process for the preparation of organic compounds useful as herbicides.

In particular this application relates to a process for preparation of compounds of formula I

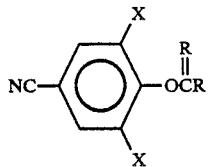

wherein R is an alkyl group and X is bromine or iodine

Use of certain esters of bromoxynil (4-hydroxy-3,5-dibromobenzonitrile) and ioxynil (4-hydroxy-3,5-diiodobenzonitrile) as herbicides has been known for many years. Examples of such derivatives are disclosed in Australia Patent No 288035.

The "Pesticide Manual" (C R Worthing, Editor; the British Crop Protection Council, 6th Edition (1979)) describes bromoxynil octanoate (2,6-dibromo 4-cyanophenyl octanoate) as a herbicide which has been used commercially for many years for the post-emergence control of broad leaved weeds in cereal crops.

Despite the considerable process advantages which would be afforded by direct preparation of these compounds from 4-hydroxybenzonitrile, it has generally been thought that, due to the incompatability of the reagents and solvents for halogenation and acylation, compounds of formula I could no be prepared without first isolating the dihalodihydroxybenzonitrile intermediate.

Recently Published Australian Patent Application 25250/84 describes a process in which bromoxynil esters are formed from 4-hydroxybenzonitrile in a single halogenated reaction solvent, halogenated solvents being compatible with both halogenating agents and acylating agents.

Although this procedure overcomes the need to isolate the intermediate, the process has several disadvantages resulting in part from the requirement that the reaction solvent be resistant to halogenation (e.g., a halogenated alkane).

We have found that it is advantageous to carry out the reaction using a solvent which may be used in the preparation of herbicidal formulations. This overcomes the time-consuming process of isolating the product and redissolving it in a suitable solvent. However, the solvents which are most useful in formulating herbicides (e.g. aromatic hydrocarbons) are generally susceptible to halogenation.

We have developed an acylation procedure which allows the compounds of formula I to be prepared without the need to isolate the intermediate 4-hydroxy-3,5-dihalobenzonitrile and which allows the compounds to be prepared in a suitable formulation solvent.

We have found that the intermediate 4-hydroxy-3,5-dihalobenzonitrile may be acylated in a two phase system comprising an aqueous phase and an organic phase, in the presence of a catalyst selected from the group consisting of nitrogen-containing bases and phase transfer catalysts.

Accordingly we provide a process for the preparation of a compound of formula I

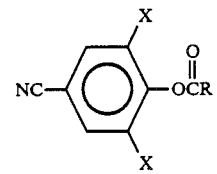

wherein R is alkyl and X is bromine or iodine, which process comprises reacting a compound of formula II with an acylating agent of formula III or IV in a two phase system comprising an aqueous phase and an organic phase comprising a water-immiscible solvent and in the presence of a catalyst selected from the group of nitrogen containing bases and phase transfer catalysts.

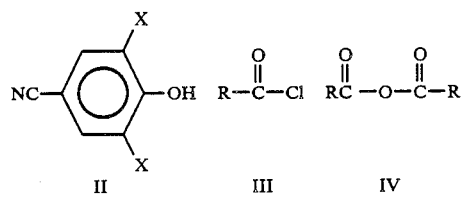

Most preferably X is bromine.

Preferably R is chosen from the group of $C_3$ to $C_{15}$ alkyl. More preferably R is chosen from $C_4$ to $C_{12}$ alkyl. Preferably the acylating agent is of formula III.

It is surprising that the esters of formula I may be prepared in the presence of an aqueous solution as it is well known that acid halides or anhydrides hydrolyse in the presence of water and the prior art procedures use dry solvents.

The acylation procedure we have developed has the further advantage of allowing the halogenation to be conducted in an aqueous mixture.

It will be understood that the use of water as a halogenation medium provides economic and handling advantages which are not present with non-aqueous systems.

Consequently, it is preferred that the hereinabove-described acylation procedure be used in combination with a halogenation process conducted in an aqueous mixture. However, it will be understood that other solvents such as acetic acid may also be used if desired.

Thus, in a preferred embodiment of the present invention, there is provided a process for the preparation of a compound of formula I which process comprises: halogenating 4-hydroxybenzonitrile in an aqueous phase to form a product of formula II; and reacting the product in a two phase system, said system comprising the aqueous phase and an organic phase comprising a water-immiscible solvent, with an acylating agent of formula III or IV in the presence of a catalyst selected from the group of nitrogen containing bases and phase transfer catalysts.

Halogenation may be effected by known methods of bromination or iodination such as using molecular halogen (i.e. bromine or iodine optimally in the presence of a Lewis acid catalyst such as ferric bromide; by using an alkali metal hypobromite; or by using another halogenating agent such as bromine chloride.

In the process of the present invention, we have found that it is particularly advantageous to use a halogenation procedure in which a halogenating agent is formed by the in situ oxidation of halide ion-containing materials.

Said halide ion-containing materials may be chosen from bromide or iodide salts of organic and inorganic cations.

Examples of organic and inorganic cations may be chosen from cations of alkali metals and alkaline earth metals, and ammonium and quaternary ammonium ions.

Preferred halide ion-containing materials may be chosen from the bromide or iodide salts of cations selected from the group of sodium, potassium, magnesium and calcium.

More preferred halide ion-containing materials are the bromide salts of sodium and calcium.

In particular we have found that advantages are provided when a halogenating agent is generated in situ by reaction of molecular chlorine with halide ion-containing material.

Accordingly, in a particularly preferred of embodiment the present invention, there is provided a process for the preparation of a compound of formula I which process comprises reacting an aqueous phase comprising 4-hydroxybenzonitrile and a halide ion-containing material with molecular chlorine to form a product of formula II, and reacting the product of formula II with an acylating agent of formula III in a two phase system comprising the aqueous phase and an organic phase comprising a water-immiscible organic solvent and in the presence of a catalyst selected from the group consisting of nitrogen-containing bases and phase transfer catalysts.

In some cases we have found it to be particularly advantageous to use bromide or iodide salts of alkaline earth metal cations and in particular calcium bromide (when X is to be bromine).

For example, we have found that the use of calcium bromide generally reduces the amount of flocculation, making separation of the phases and handling in general much easier. Furthermore, calcium bromide is generally less expensive than alternatives such as sodium bromide.

Examples of suitable water-immiscible solvents may include hydrocarbons, chlorinated hydrocarbons such as chloroform, and aromatic hydrocarbons such as benzene, xylene, toluene and mesitylene.

As hereinbefore discussed, the process of the present invention has the advantage of allowing the compounds of formula I to be prepared in solvents suitable for the particular herbicide formulation. Solvents useful in this regard are selected from aliphatic and aromatic hydrocarbons and particularly preferred solvents are xylene and toluene. However, it will be understood by those skilled in the art that the present invention will allow a certain flexibility in the choice of the solvent, and other solvents such as chlorinated hydrocarbons may be used if desired.

The catalyst may be selected from, nitrogen-containing bases and phase transfer catalysts. Examples of nitrogen-containing bases include tertiary amines, nitrogen-containing heteroaromatics alkyl-substituted nitrogen containing aromatics. Examples of phase transfer catalysts include quaternary ammonium salts phosphonium salts, crown ethers, and cryptates. Preferred phase transfer catalysts are quaternary ammonium salts and phosphonium salts.

Preferred catalysts include: nitrogen-containing heteroaromatics of 5 or 6 constituent ring members optionally substituted with one or more alkyl groups; and compounds of formula selected from the groups of formulas V, VI and VII

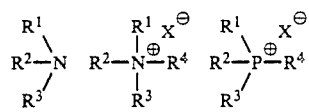

wherein $R^1$, $R^2$ and $R^3$ are independently selected from aliphatic hydrocarbon radicals of from 1 to 20 carbon atoms, phenyl-substituted $C_1$ to $C_{10}$ alkyl and pyridyl substituted $C_1$ to $C_{10}$ alkyl.

$R^4$ is selected from $C_1$ to $C_6$ alkyl and benzyl and X is an organic or inorganic anion.

Preferred nitrogen-containing heteroaromatics include pyridine optionally substituted with from 1 to 3 $C_1$ to $C_6$ alkyl groups.

Preferred catalysts of formula V and VI are those compounds wherein $R^1$ is selected from the group consisting of $C_1$ to $C_{20}$ alkyl and benzyl;

$R^2$, $R^3$ and $R^4$ are selected from $C_1$ to $C_6$ alkyl and benzyl and X is bromine or chlorine.

Specific examples of catalysts include tri-n-butylamine, pyridine, N,N-dimethylaminopyridine, benzyltributylammonium chloride, tetra-n-butyl-ammonium chloride, decyldimethylbenzylammonium chloride, cetyltrimethylammonium chloride and tri-n-butylmethylphosphonium chloride.

Generally the amount of catalyst will be in the range $10^{-4}$ to 0.5 mole equivalent of catalyst based on halogenated 4-hydroxybenzonitrile (i.e. compound of formula II) and preferably 0.001 to 0.1 mole equivalent. We have found that 0.05 equivalent or less is generally adequate to provide an efficient reaction procedure under mild conditions. However, if desired, larger amounts of base catalyst, (as much as 0.5 mole equivalent or more) may be used.

The amounts of reagents used in the process of the present invention may be determined by those skilled in the art having reference to the stoichiometry of the reactions involved and/or by monitoring the formation of halogenated, and subsequently acylated, products using known analytical techniques such as thin layer chromatography or G.L.C.

For example, where bromination is effected by in situ oxidation of a metal bromide using molecular chlorine, the stoichiometry for conversion of 1 mole of 4-hydroxybenzonitrile will involve 2 mole of bromide ion, 2 mole of molecular chlorine and one mole of acylating agent.

In general it is preferred to use a slight excess of reagents (for example, 2.2 molar equivalents of bromide ion and molecular chlorine and 1.1 molar equivalents of acylation agent) although larger excesses may be used if desired.

The conditions required to effect the reactions involved in the process of the present invention will vary according to the nature of the reactants and the solvent used. The reactions may be carried out at ambient temperature; however, heat may be applied during the reaction or after the addition of the acylating agent.

Usually the reaction temperature will be in the range of from 0° to 200° C. (preferably 0° to 100°) and a reaction time will generally be between 0.5 and 20 hours.

However, higher or lower reaction temperatures and/or shorter or longer times may be employed if desired. In general, the reaction time necessary may be determined by monitoring the course of the reactions.

Generally we have found that the reaction proceeds more efficiently if the aqueous solution is made alkaline prior to the addition of the acylating agent, for example by the addition of greater than 2 mole equivalents based on 4-hydroxybenzonitrile of sodium hydroxide.

In particular, in many cases we have found that good results are obtained where the aqueous mixture comprising 4-hydroxybenzonitrile and halide ion-containing material further comprises at least two mole equivalents based on 4-hydroxybenzonitrile of a metal hydroxide. (e.g. sodium hydroxide) on In a typical example of the process of the present invention, chlorine gas (approx. 2.2 mole equivalents) is bubbled through an aqueous solution comprising an alkali metal bromide (approx. 2.2 mole equivalents) or alkaline earth metal bromide (approx. 1.1 mole equivalents) and 4-hydroxybenzonitrile (1 mole equivalent), and the mixture is stirred until formation of bromoxynil is substantially complete. The acid generated during the halogenation is neutralised and an excess of base is added (e.g. 1 mole excess). A water-immiscible organic solvent (e.g. xylene) is added and an acid chloride (1.1 mole equivalents) and catalyst are also added. The mixture is then stirred until the reaction is substantially complete. In a preferred alternative, the initial aqueous solution comprises 3 mole equivalents of base (e.g. sodium hydroxide), obviating the need to add base during the course of the reaction.

It may be preferred to add the acid chloride slowly for example over a period in the range of 5 minutes to 5 hours. Unlike previously used procedures for preparation of bromoxynil esters such as bromoxynil octanoate, the present invention enables preparation from 4-hydroxybenzonitrile without the need to isolate and dry the bromoxynil intermediate. This offers a considerable cost and time saving for large scale preparation.

The in situ halogenation procedure provides several time and cost saving advantages.

The reaction provides maximum utilisation of bromine (or iodine) and it avoids many of the disadvantages of other techniques which require noxious bromine gas or the dual handling of both bromine gas and chlorine gas. Furthermore, unlike many halogenation techniques, the brominating or iodinating agent is generated in situ and hence preformation of the agent is not required.

We believe this procedure for halogenation of 4-hydroxybenzonitrile is novel. Hence in a further embodiment of this invention there is provided a process for the halogenation of 4-hydroxybenzonitrile which process comprises reacting an aqueous mixture comprising 4-hydroxybenzonitrile and halide ion- containing material as hereinbefore defined with molecular chlorine.

For the preparation of bromoxynil (ioxynil) the molar ratios of bromide (iodide) to 4-hydroxybenzonitrile and chlorine to 4-hydroxybenzonitrile are generally in the range 1.9:1 to 2.5:1. Good results are generally obtained when ratio is about 2.2:1.

The invention is now demonstrated but not limited to the following examples:

EXAMPLE 1

A mixture of 3,5-dibromo-4-hydroxybenzonitrile (27.69 g) sodium hydroxide (4.08 g), sodium chloride (43.4 g) and water (125 ml) was stirred at room temperature for 15 minutes. Toluene (30 ml) and benzyltributyl ammonium chloride (1.57 g) was added, and a solution of octanoyl chloride (17.06 g) in toluene (30 ml) was slowly added to the stirred mixture over a half an hour while the temperature was maintained at 20° C. After addition was completed, the mixture was stirred for 1 hour and the phases allowed to separate. After removing the aqueous phase, the organic phase was washed with water, then with 5% aqueous $Na_2O_3$ and again with water. The solution was dried over $Na_2O_3$ and evaporated to dryness, yielding 2,6-dibromo-4-cyanophenyl octanoate (40.08 g, 99.5%) as a brown crystalline solid.

EXAMPLE 2

To a 2 L flask fitted with a condenser, mechanical stirrer, condenser, gas inlet port, and a sodium hydroxide scrubber was charged 4-hydroxybenzonitrile (62.5 g, 525 mmol), calcium bromide monohydrate (125.9 g, 577 mmol), and water (700 mls). Into the resulting suspension was bubbled chlorine gas (85 g, 1197 mmol) at such a rate that the temperature did not rise above 50° C. and that bromine fu=° were not visible. After chlorine addition was complete, the thick suspension was stirred for one hour. To the suspension was charged a 46% w/w sodium hydroxide solution (140 g, 1610 mmol), and after half an hour of stirring, toluene (300 mls) and benzyltributylammonium chloride (8.25 g, 26 mmol) were added. Octanoyl chloride (89.6 g, 551 mmol) was added to the rapidly stirred solution over half an hour, while the temperature was kept below 30° C. After addition was complete, stirring was continued for one hour. Stirring was stopped and the phases separated. The toluene layer was washed in order with 15% brine solution (200 mls), 5% bicarbonate (200 mls), and 15% brine solution (200 mls) and was dried by azeotropic distillation of water to give 430 g of a brick red solution of bromoxynil octanoate.

Analysis by g.l.c. showed; purity +95%, assay 46.5% w/w to give a yield of 94.7%.

EXAMPLE 3

Procedure identical to the above except that the calcium bromide was replaced by sodium bromide (119 g, 1.15 mmoles). A good conversion to bromoxynil octanoate was observed.

EXAMPLE 4

Preparation of (2,6-Dibromo-4-cyanophenyl) octanoate

To a 1 L flask fitted with a condenser, mechanical stirrer, condenser, gas inlet port, and a sodium hydroxide scrubber was charged 4-hydroxybenzonitrile (62.5 g, 525 mmol), calcium bromide monohydrate (125.9 g, 577 mmol), and water (350 mls). To the resulting suspension was slowly added a 46% w/w sodium hydroxide solution (160 g, 1838 mmol) such that the temperature did not rise above 30° C. Chlorine gas (85 g, 1197 mmol) was bubbled into the suspension at such a rate that the temperature did not rise above 50° C. and that the bromine fumes were not visible. When the chlorine addition was complete, the suspension was stirred for one hour. To the suspension was charged toluene (300 mls), and octanoyl chloride (89.6 g, 551 mmol) was then added to the rapidly-stirred solution over half an hour, while the temperature was kept below 30° C. When addition was complete, stirring was continued for an hour. Stirring was stopped, the phases were separated and the toluene layer was washed with 15% brine solution (200 mls). The toluene layer was dried by azeotropic distillation of water to give 330 g of a brick red solution of bromoxynil octanoate.

Analysis by g.l.c. showed; purity 92% w/w; assay 57% w/w to give a yield of 89%.

EXAMPLE 5

Preparation of 3,5-Dibromo-4-hydroxybenzonitrile

The procedure of Example 3 was repeated, except that after chlorine addition and one hour of stirring, the suspension was acidified with 6% w/w hydrochloric acid solution until pH 3 or lower was achieved. The resulting solid was filtered off and washed several times with warm water. It was then dried in a vacuum oven to give 192 g of crude product; 98% yield. Purity unknown.

EXAMPLE 6

Preparation of 3,5-Diiodo-4-hydroxybenzonitrile

The procedure of Example 4 was repeated except that calcium bromide was replaced with sodium iodide (173.7 g, 577 mmol). The final result was 154 g of crude ioxynil, 80% yield. Purity unknown.

EXAMPLE 7

To a 2 L flask fitted with a condenser, mechanical stirrer, gas inlet port and a sodium hydroxide scrubber was charged 4-hydroxybenzonitrile (62.5g, 525 mmol), calcium bromide monohydrate (125.9 g, 577 mmol), and water 1200 ml). Chlorine gas (85 g, 1197 mmol) was bubbled into the suspension at such a rate that the temperature did not exceed 50° C. and bromine fumes were not visible. When the reaction was complete, sodium metabisulphite solution (5%, 100 ml) was added to the mixture and the suspension stirred for 15 minutes. The crude bromoxynil was filtered and washed well with water.

Yield after drying 141.5 g.

EXAMPLE 8

To a mixture comprising sodium hydroxide (1.55 g), water (45 ml) and 3,5-dibromo-4-hydroxybenzonitrole (10 g) was added benzyltributylammonium chloride (0.57 g) and xylene (10.8 ml). The mixture was stirred and calcium chloride (14.1 g) was added. This was followed by the slow addition (over 30 minutes) of a mixture of octanoyl chloride (6.16 g) and xylene (10.8 ml). The mixture was stirred for 1 hour and the phases allowed to separate. The organic phase was washed with brine (15%) and dried to provide a good yield of bromoxynil octanoate.

EXAMPLES 9–12

The procedure of Example 8 was repeated substituting other solvents and catalysts for the xylene and the benzylbutylammonium of that example according to the following table:

| Example | Organic Solvent | *Catalyst |
| --- | --- | --- |
| 9 | toluene | pyridine |
| 10 | toluene | tri-n-butylamine |
| 11 | xylene | [$C_{16}$-$C_{18}$ alkyl] trimethylammonium chloride |
| 12 | xylene | decyldimethyl-benzylammonium chloride |

*The amount of catalyst used was 0.05 molar equivalents based on bromoxynil.

In all cases, a good conversion to bromoxynil octanoate was observed.

We claim:

1. A process for the preparation of a compound of formula I:

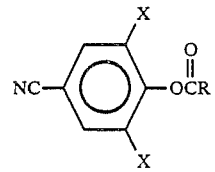

wherein R is alkyl and X is selected from bromine and iodine which process comprises preparing a compound of formula II

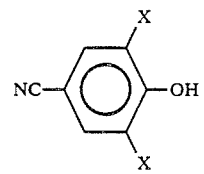

by halogenating 4-hydroxybenzonitrile in an aqueous phase using bromine or iodine to halogenate said 4-hdyroxybenzonitrile, said bromine or iodine being formed by in situ oxidation of a bromide- or iodide-ion containing material with molecular chlorine and then reacting the resulting compound II, without isolating the same, with an acylating agent selected from formulas III and IV

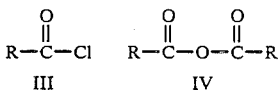

in a two phase system comprising an aqueous phase and an organic phase comprising a water-immiscible, aliphatic or aromatic hydrocarbon or chlorinated hydrocarbon solvent and in the presence of a catalyst selected from the group consisting of nitrogen containing bases and phase transfer catalysts, the resulting product I being suitable for use in the preparation of herbicidal formulation without the need for isolating the same.

2. A process according to claim 1 wherein R is $C_3$ to $C_{15}$ alkyl.

3. A process according to claim 1 wherein R is $C_4$ to $C_{12}$ alkyl.

4. A process according to claim 1 wherein X is bromine

5. A process according to claim 1 wherein the acylating agent is a compound of formula III.

6. A process according to claim 1 wherein said halide ion containing materials are selected from bromide and iodide salts of organic and inorganic cations said cations being selected from the group consisting of alkali metal cations, alkaline earth metal cations, ammonium cations, and quaternary ammonium cations.

7. A process according to claim 6 wherein said cations are selected from the group consisting of sodium, potassium, magnesium and calcium.

8. A process according to claim 1 wherein the molar ratios of halide ion to 4-hydroxybenzonitrile and chlorine to 4-hydroxybenzonitrole are both in the range 1.9:1 to 2.5:1.

9. A process according to claim 1 wherein the water immiscible solvent is selected from the group consisting of aliphatic, hydrocarbons aromatic hydrocarbons and chlorinated hydrocarbons.

10. A process according to claim 9 wherein the solvent is selected from xylene and toluene.

11. A process according to claim 1 wherein the catalyst is selected form the group consisting of tertiary amines, nitrogen containing heteroaromatics, alkyl substituted nitrogen containing aromatics, quaternary ammonium salts, phosphonium salts, crown ethers and cryptates.

12. A process according to claim 11 wherein the catalyst is selected from the group consisting of : nitrogen containing heteroaromatics of 5 or 6 constituent ring numbers optionally substituted with one or more alkyl groups; and compounds of formula selected from the group of formulas V, VI and VII

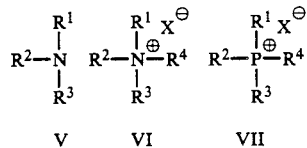

wherein:
$R^1$, $R^2$ and $R^3$ are independently selected from the aliphatic hydrocarbon radicals of from 1 to 20 carbon atoms, phenyl-substituted $C_1$ to $C_{10}$ alkyl, and pyridyl-substituted $C_1$ to $C_{10}$ alkyl;
$R^4$ is selected from $C_1$ to $C_6$ alkyl and benzyl; and
X is an inorganic or organic anion.

13. A process according to claim 12 wherein the catalyst is selected from the group consisting of : pyridine optionally substituted with from 1 to 3 $C_1$ to $C_6$ alkyl groups and compounds of formulas V and VI wherein:
$R^1$ is selected from $C_1$ to $C_{20}$ alkyl and benzyl;
$R^2$, $R^3$ and $R^4$ are selected from $C_1$ to $C_6$ alkyl and benzyl; and
X is selected from bromine and chlorine.

14. A process according to claim 1 wherein the catalyst is present at a concentration in the range of $1 \times 10^{-4}$ to 0.5 mole equivalents based on the compound of formula II.

15. A process according to claim 14 wherein the range is 0.001 to 0.1 mole equivalents.

16. A process according to claim 1 wherein the temperature is in the range of 0° to 200° C.

* * * * *